(12) United States Patent
Yoshida

(10) Patent No.: US 11,647,901 B2
(45) Date of Patent: May 16, 2023

(54) ENDOSCOPE AND IMAGE PICKUP APPARATUS

(71) Applicant: OLYMPUS CORPORATION, Tokyo (JP)

(72) Inventor: Kazuhiro Yoshida, Okaya (JP)

(73) Assignee: OLYMPUS CORPORATION, Tokyo (JP)

( * ) Notice: Subject to any disclaimer, the term of this patent is extended or adjusted under 35 U.S.C. 154(b) by 874 days.

(21) Appl. No.: 16/662,599

(22) Filed: Oct. 24, 2019

(65) Prior Publication Data

US 2020/0054190 A1 Feb. 20, 2020

Related U.S. Application Data

(63) Continuation of application No. PCT/JP2017/016348, filed on Apr. 25, 2017.

(51) Int. Cl.
*A61B 1/05* (2006.01)
*A61B 1/00* (2006.01)
(Continued)

(52) U.S. Cl.
CPC .......... *A61B 1/051* (2013.01); *A61B 1/00009* (2013.01); *A61B 1/00013* (2013.01);
(Continued)

(58) Field of Classification Search
CPC ... A61B 1/00011; A61B 1/00018; A61B 1/04; A61B 1/042; A61B 1/00163;
(Continued)

(56) References Cited

U.S. PATENT DOCUMENTS 6,313,456 B1 * 11/2001 Miyashita ......... H01L 27/14618
250/239
10,217,782 B2 * 2/2019 Maeda .............. H01L 27/14683
(Continued)

FOREIGN PATENT DOCUMENTS

JP 2000-210252 A 8/2000
JP 4589659 B2 9/2010
(Continued)

OTHER PUBLICATIONS

International Search Report dated Aug. 1, 2017 received in PCT/JP2017/016348.

*Primary Examiner* — Ryan N Henderson
*Assistant Examiner* — Pamela F Wu
(74) *Attorney, Agent, or Firm* — Scully, Scott, Murphy & Presser, P.C.

(57) ABSTRACT

An endoscope includes an image pickup apparatus, and the image pickup apparatus includes an imager includes an external electrode, a stacked device, a top electrode on a top surface, and a bottom electrode on a bottom surface, a three-dimensional wiring board having a first zone to which the external electrode is bonded, a second zone to which the top electrode or the bottom electrode is bonded, a third zone to which the top electrode or the bottom electrode is bonded, and a fifth zone arranged on a side surface of the stacked device, wherein the top surface, the bottom surface, and at least two side surfaces of the stacked device are covered with the wiring board.

14 Claims, 10 Drawing Sheets

(51) Int. Cl.
*G06T 7/00* (2017.01)
*H01L 25/065* (2023.01)

(52) U.S. Cl.
CPC ............ *A61B 1/00096* (2013.01); *A61B 1/05* (2013.01); *G06T 7/0012* (2013.01); *H01L 25/0657* (2013.01); *H01L 2225/06541* (2013.01)

(58) Field of Classification Search
CPC .............. A61B 1/000205; A61B 1/051; A61B 1/05–053; A61B 1/00096; A61B 1/0011; H01L 25/0657; H01L 25/074; H01L 25/075; H01L 25/0756; H02L 25/00
USPC .................................. 600/101, 109, 110, 160
See application file for complete search history.

(56) References Cited

U.S. PATENT DOCUMENTS

| | | | |
|---|---|---|---|
| 2006/0109368 A1* | 5/2006 | Ayrenschmalz | H04N 5/2253 348/340 |
| 2015/0228678 A1* | 8/2015 | Yoshida | H01L 27/1464 600/110 |
| 2017/0280969 A1* | 10/2017 | Levy | A61B 1/00177 |

FOREIGN PATENT DOCUMENTS

| | | |
|---|---|---|
| JP | 2013-030593 A | 2/2013 |
| JP | 2013-219511 A | 10/2013 |
| WO | 2016/189679 A1 | 12/2016 |
| WO | 2016/203828 A1 | 12/2016 |

* cited by examiner

ENDOSCOPE AND IMAGE PICKUP APPARATUS

CROSS REFERENCE TO RELATED APPLICATION

This application is a continuation application of PCT/JP2017/016348 filed on Apr. 25, 2017, the entire contents of which are incorporated herein by this reference.

BACKGROUND OF INVENTION

1. Field of the Invention

The present invention relates to an endoscope that includes an image pickup apparatus including an imager, a stacked device, and a wiring board, and also relates to an image pickup apparatus including an imager, a stacked device, and a wiring board.

2. Description of the Related Art

An endoscope includes an insertion portion, an operation portion, and a universal cord. When an image pickup module is used which is configured to perform primary processing on an image pickup signal outputted from an imager disposed at a distal end portion of the insertion portion by a plurality of semiconductor devices arranged immediately proximal to the imager, signal degradation caused by an influence from reduction in a diameter of the distal end portion, noise at the time of signal transmission using a signal cable, and the like is avoided, and a high quality image can be displayed.

In order to contain a plurality of semiconductor devices in a small space, and also to reduce a parasitic capacitance caused by wiring, Japanese Patent Application Laid-Open Publication No. 2013-30593 discloses a stacked device obtained by stacking a plurality of semiconductor devices via a through-silicon via.

SUMMARY OF THE INVENTION

An endoscope according to an embodiment of the present invention includes an image pickup apparatus, and the image pickup apparatus includes an imager including a light receiving surface and a rear surface on a reverse side of the light receiving surface, and an external electrode disposed on the rear surface, a stacked device including a plurality of devices stacked in a direction intersecting an optical axis of the imager, having a rectangular parallelepiped shape including a top surface, a bottom surface on an opposite side to the top surface, and four side surfaces, and including a top electrode disposed on the top surface and a bottom electrode disposed on the bottom surface, a wiring board including a first zone to which the external electrode is bonded, a second zone to which the top electrode or the bottom electrode is bonded, a third zone to which the top electrode or the bottom electrode that is not bonded to the second zone is bonded, and a fifth zone arranged on a first side surface among the four side surfaces of the stacked device, the first zone, the second zone, the third zone, and the fifth zone being consecutively disposed, and a signal cable bonded to a zone other than the first zone of the wiring board, in which the top surface, the bottom surface, and at least two side surfaces including the first side surface among the four side surfaces are covered with the wiring board in the stacked device.

An image pickup apparatus according to another embodiment includes an imager including a light receiving surface and a rear surface on a reverse side of the light receiving surface, and an external electrode disposed on the rear surface, a stacked device including a plurality of devices stacked in a direction intersecting an optical axis of the imager, having a rectangular parallelepiped shape including a top surface, a bottom surface on an opposite side to the top surface, and four side surfaces, and including a top electrode disposed on the top surface and a bottom electrode disposed on the bottom surface, a wiring board including a first zone to which the external electrode is bonded, a second zone to which the top electrode or the bottom electrode is bonded, a third zone to which the top electrode or the bottom electrode that is not bonded to the second zone is bonded, and a fifth zone arranged on a first side surface among the four side surfaces of the stacked device, the first zone, the second zone, the third zone, and the fifth zone being consecutively disposed, and a signal cable bonded to a zone other than the first zone of the wiring board, in which the top surface, the bottom surface, and at least two side surfaces including the first side surface among the four side surfaces are covered with the wiring board in the stacked device.

DETAILED DESCRIPTION OF THE PREFERRED EMBODIMENTS

First Embodiment

Figure 1A:
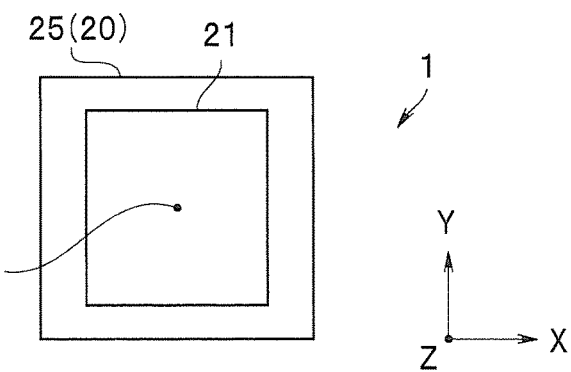
FIG. 1A is a front view of an image pickup module according to a first embodiment.

As illustrated in FIGS. 1A to 1D, an image pickup module 1 serving as an image pickup apparatus according to the present embodiment includes an imager 20, a cover glass 25, a wiring board 10, a stacked device 30, and a signal cable 40.

Drawings based on respective embodiments are schematic drawings. Note that a relationship between a thickness and a width of each of sections, and a thickness ratio and the like of each of the sections are different from actual configurations. A part where a mutual dimensional relationship or ratio is different between mutual drawings may be included in some cases. Illustration of part of components and assignment of reference signs may be omitted in some cases. Note that the following drawings are represented based on an XYZ-Cartesian coordinate system, in which a direction of an optical axis O of the imager 20 is set as a Z-axis.

Figure 1B:
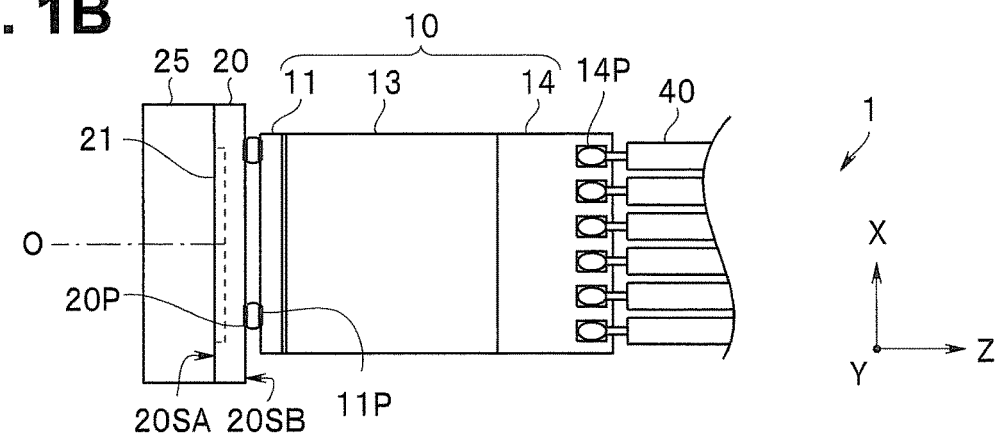
FIG. 1B is a top view of the image pickup module according to the first embodiment.
Figure 1C:
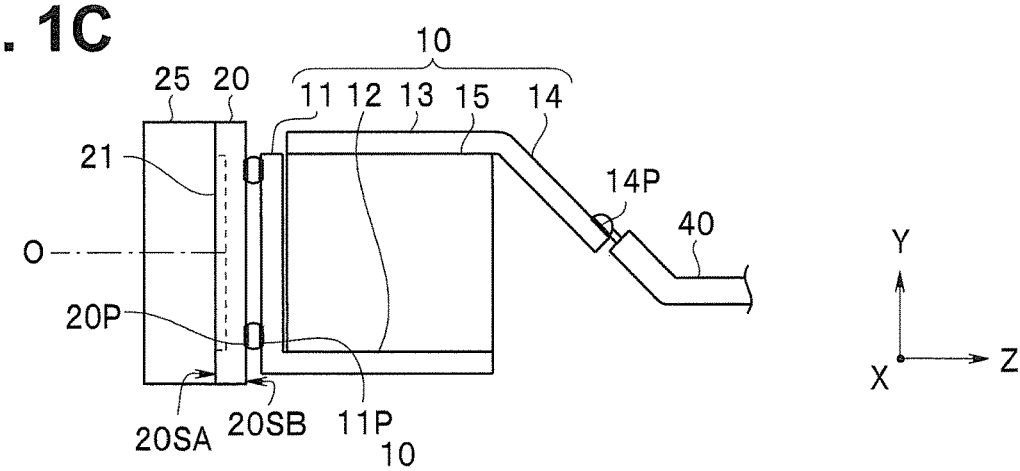
FIG. 1C is a right side view of the image pickup module according to the first embodiment.
Figure 1D:
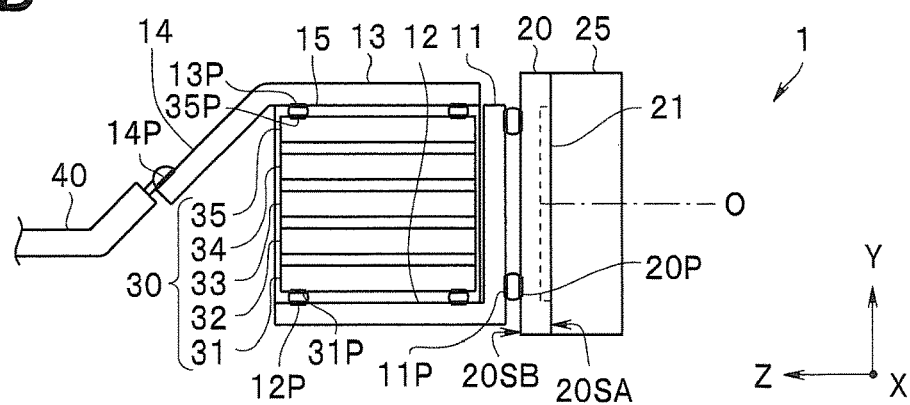
FIG. 1D is a left side view of the image pickup module according to the first embodiment.

FIG. 1A is a front view, in which a front side on a sheet plane is an optical axis forward direction with regard to the Z-axis. FIG. 1B is a top view, in which the front side on the sheet plane is an upward direction with regard to a Y-axis intersecting the optical axis. FIG. 1C is a right side view, in which the front side on the sheet plane is a right direction with regard to an X-axis intersecting the optical axis. FIG. 1D is a left side view, in which the front side on the sheet plane is a left direction with regard to the X-axis. An X-direction may be a vertical direction, and a Y-direction may be a horizontal direction.

Figure 2:
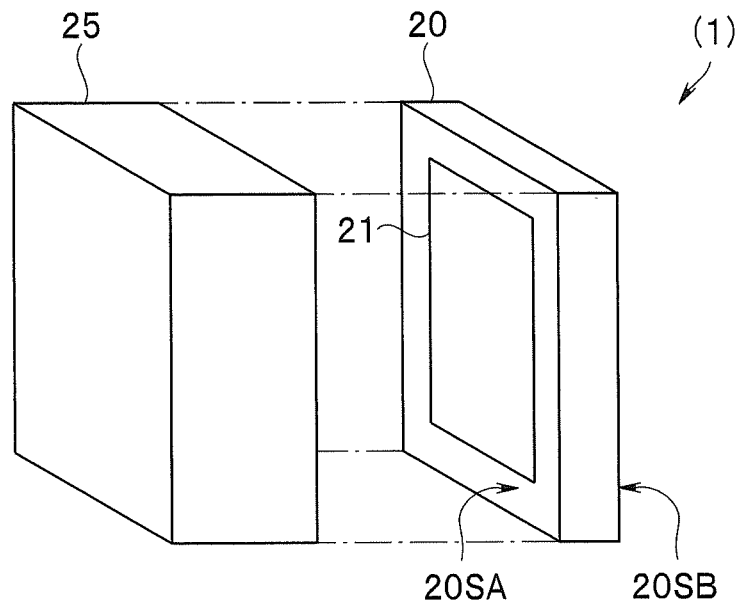
FIG. 2 is an exploded perspective view of an image pickup portion of the image pickup module according to the first embodiment.

As illustrated in FIG. 2, the imager 20 is an imager including a light receiving surface 20SA on which a light receiving portion 21 composed of a charge-coupled device (CCD) or a complementary metal-oxide semiconductor (CMOS) image pickup portion is disposed, and a rear surface 20SB on a reverse side of the light receiving surface 20SA. The light receiving portion 21 includes a light receiving region where a plurality of photodiodes are formed, a color filter (not illustrated) disposed on the light receiving region, and a micro lens (not illustrated) disposed on the color filter. The light receiving portion 21 is connected to a plurality of external electrodes 20P disposed on the rear surface 20SB via a through-silicon via (not illustrated).

The cover glass 25 is bonded to the light receiving surface 20SA of the imager 20 via an adhesion layer (not illustrated). Note that the cover glass 25 is not an essential component of the image pickup module 1. On the contrary, an optical unit constituted by a plurality of optical devices including a cover glass may also be disposed on the light receiving surface 20SA.

Figure 3:
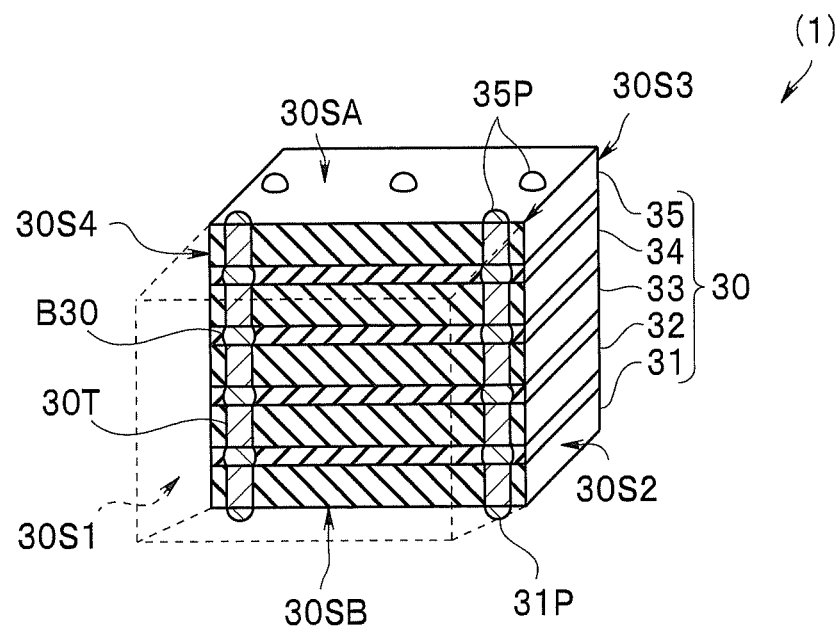
FIG. 3 is a partial cross sectional view of a stacked device of the image pickup module according to the first embodiment.

As illustrated in FIG. 3, a stacked device (stacked chip) 30 is constituted by stacking a plurality of flat plate semiconductor devices (semiconductor chips) 31 to 35 in the vertical direction (Y-direction) intersecting the optical axis O of the imager 20, and has a rectangular parallelepiped shape including a top surface 30SA serving as a first surface, a bottom surface 30SB serving as a second surface on a side opposite to the top surface 30SA, and four side surfaces 30S1 to 30S4. A plurality of top electrodes 35P are disposed on the top surface 30SA, and a plurality of bottom electrodes 31P are disposed on the bottom surface 30SB.

The stacked device 30 is each fabricated by cutting process of a bonded wafer obtained by stacking and bonding a plurality of semiconductor wafers including the semiconductor device 31, the semiconductor device 32, the semiconductor device 33, the semiconductor device 34, or the semiconductor device 35. The four side surfaces 30S1 to 30S4 of the stacked device 30 corresponding to a rectangular parallelepiped shape are cut surfaces.

The respective semiconductor devices 31 to 35 are connected to one another via a through-silicon via (TSV) 30T and a bump B30. Therefore, the semiconductor devices 31 to 35 have a small parasitic capacitance of wiring between the devices and are also small-sized. Sections between the respective semiconductor devices 31 to 35 are sealed by sealing resin. For example, the semiconductor device 31 is a device including a thin film capacitor, the semiconductor device 32 is a filter circuit device, and the semiconductor device 33 is an analog-to-digital (AD) conversion circuit device. The number of devices included in the stacked device 30 is, for example, 2 or higher and 10 or lower.

Note that the stacked device 30 has a complete rectangular parallelepiped shape, but a "rectangular parallelepiped" shape according to the present invention also includes a substantially rectangular parallelepiped shape in which a corner section is chamfered or curved.

Note that dimensions (external sizes) of the image pickup module 1 intersecting the optical axis O of the imager 20 is 1 mm square or smaller, for example, 600 μm×600 μm. External sizes of the stacked device 30 to which the wiring board 10 is bonded are designed to be smaller than or equal to the external sizes of the imager 20. In other words, the image pickup module 1 is an ultra-compact image pickup module specialized for endoscope.

In the image pickup module 1, the imager 20, the stacked device 30, and the signal cable 40 are electrically connected to one another by the single wiring board 10. For this reason, the image pickup module 1 is ultra compact, but the structure is simple, and fabrication is easy.

Figure 4:
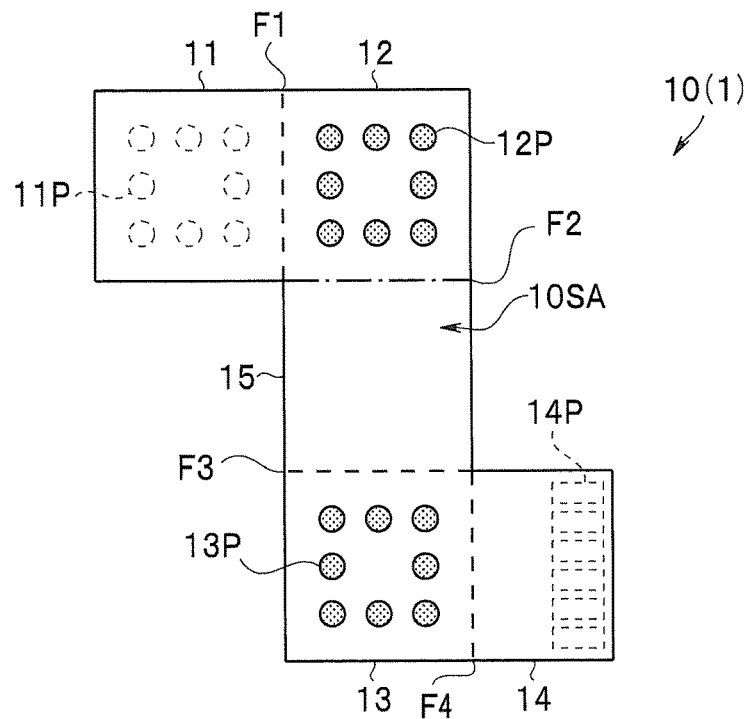
FIG. 4 is a development diagram of a wiring board of the image pickup module according to the first embodiment.

As illustrated in FIG. 4, the wiring board 10 includes a first zone 11 in which a plurality of first electrodes 11P are disposed, a second zone 12 in which a plurality of second electrodes 12P are disposed, a third zone 13 in which a plurality of third electrodes 13P are disposed, a fourth zone 14 in which a plurality of fourth electrodes 14P are disposed, and a fifth zone 15. The electrodes are connected to one another via wiring that is not illustrated in the drawing.

The fifth zone 15 arranged on the first side surface 30S1 among the four side surfaces of the stacked device 30 connects the second zone 12 and the third zone 13. The first zone 11, the second zone 12, the fifth zone 15, the third zone 13, and the fourth zone 14 are consecutively disposed in the above-stated order. In other words, the above-mentioned plural zones are constituted by the consecutively disposed and integrated wiring board 10.

The wiring board 10 is a double-sided wiring board in which the second electrodes 12P and the third electrodes 13P are disposed on a first main surface 10SA, and the first electrodes 11P and the fourth electrodes 14P are disposed on a second main surface 10SB on a reverse side of the first main surface 10SA. The wiring board 10 may also be a multilayer wiring board in which wiring is further disposed in an intermediate layer between the first main surface 10SA and the second main surface 10SB.

Figure 5:
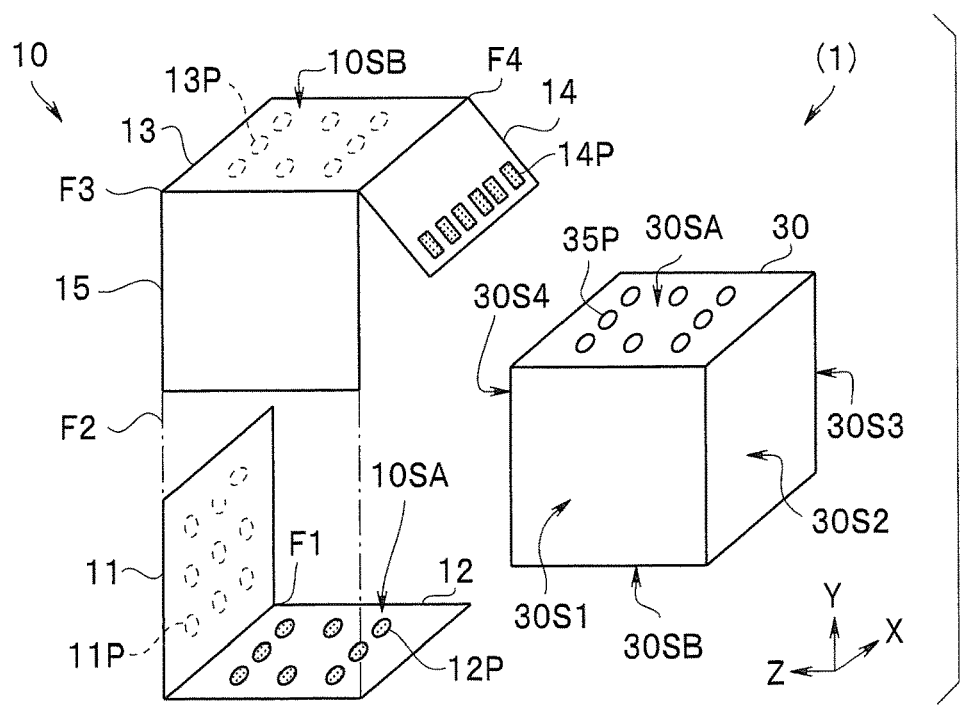
FIG. 5 is an exploded perspective view of the wiring board and the stacked device of the image pickup module according to the first embodiment.

As illustrated in FIG. 5, the wiring board 10 having flexibility where polyimide or the like is used as a base substance is folded via folded sections F1 to F4 between the zones. The first zone 11 serving as a flat surface and the second zone 12 serving as a flat surface are orthogonally arranged via the folded section F1 at 90 degrees where a folding angle is 90 degrees or lower. In other words, the wiring board 10 is folded at the folding angle of 90 degrees or lower in the respective sections between the first zone 11, the second zone 12, the third zone 13, and the fourth zone 14.

As illustrated in FIG. 1D and the like, the external electrodes 20P of the imager 20 are bonded to the first electrodes 11P in the first zone 11. The bottom electrodes 31P of the stacked device 30 are bonded to the second electrodes 12P in the second zone 12. The top electrodes 35P of the stacked device 30 are bonded to the third electrodes 13P in the third zone 13. Connection between the second electrodes 12P in the second zone 12 and the bottom electrodes 31P of the stacked device 30 and connection between the third electrodes 13P in the third zone 13 and the top electrodes 35P of the stacked device 30 are performed by using, for example, bonding using soldering, conductive adhesive, anisotropic conductive paste (ACP), or an anisotropic conductive film (ACF), ultrasound bonding using both ultrasound and heat, or thermo compression bonding based on non-conductive paste (NCP) or a non-conductive film (NCF).

The signal cable 40 is bonded to the fourth electrodes 14P in the fourth zone 14. Bonding using soldering, conductive adhesive, or the like, or the ultrasound bonding using both ultrasound and heat is used for the bonding between the fourth electrodes 14P in the fourth zone 14 and the signal cable 40, for example.

Since the first zone 11 in which the external electrodes 20P of the imager 20 are bonded is a different zone from the second zone 12, the third zone 13, and the fourth zone 14, there is no risk that heat for bonding zones other than the first zone 11 is applied to the imager 20. Particularly, there is no risk that the light receiving portion 21 of the imager 20 where the micro lens and the color filter are disposed is adversely affected. Further, after the bonding of the zones other than the first zone 11 is performed, the first zone 11 can be lastly bonded to the imager 20. For this reason, the image pickup module has high reliability since there is not risk that the imager 20 is degraded by heat.

The single wiring board 10 of the flat plate (two-dimensional structure) is folded via the folded sections F1 to F4 to turn into a three-dimensional (3D structure) wiring board that connects the imager 20, the stacked device 30, and the signal cable 40. For this reason, the wiring board 10 is inexpensive, and also fabrication is easy.

Note that the fifth zone 15 having substantially a same size as the first side surface 30S1 of the stacked device 30 is arranged along the first side surface 30S1 in the image pickup module 1. The second zone 12 and the third zone 13 have substantially a same size as the top surface 30SA and the bottom surface 30SB of the stacked device 30. In a case where the stacked device 30 has a cubic shape, the fifth zone 15 and the second zone 12 have a same size. To put it the other way around, in a case where the stacked device 30 does not have a cubic shape, the fifth zone 15 and the second zone 12 have different sizes.

In FIG. 5 and the like, the folded sections F1 to F4 are simplified and represented as lines but are constituted by curved surfaces having areas in actuality. The wiring board 10 may also be a rigid flexible wiring board in which the respective zones are composed of glass epoxy resin or the like having no flexibility when the wiring board includes the integrated folded sections having flexibility. An electronic part such as a chip capacitor may also be mounted to the fourth zone 14.

The top surface 30SA, the bottom surface 30SB, and the three side surfaces 30S1, 30S3, and 30S4 including the first side surface 30S1 among the four side surfaces 30S1 to 30S4 are covered with the wiring board 10 in the stacked device 30.

Modifications of First Embodiment

Since image pickup modules 1A to 1G according to modifications of the first embodiment are similar to the image pickup module 1 and have same advantages, components having same functions are assigned with same reference signs, and descriptions of the above-mentioned components are omitted.

First Modification of First Embodiment

A wiring board 10A of the image pickup module 1A according to the present modification is the same as the wiring board 10 of the image pickup module 1. However, the wiring board 10A and the wiring board 10 have different positional relationships with the stacked device 30.

Figure 6:
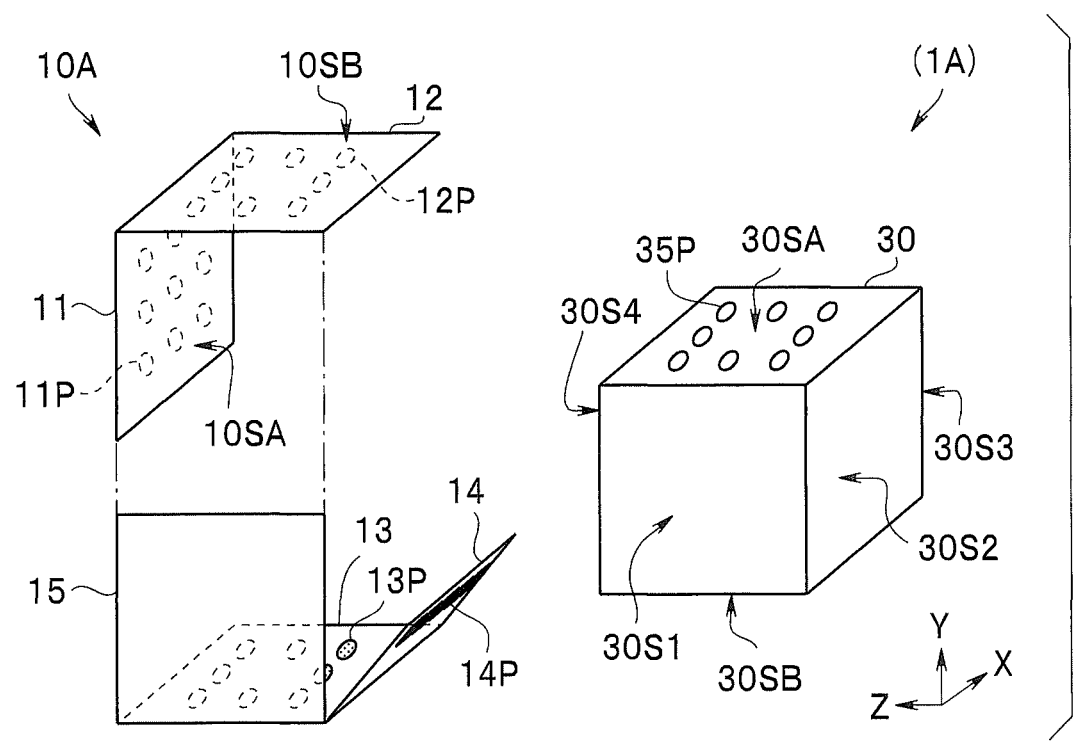
FIG. 6 is an exploded perspective view of a wiring board and a stacked device of an image pickup module according to a first modification of the first embodiment.

In other words, as illustrated in FIG. 6, the top electrodes 35P of the stacked device 30 are bonded to the second electrodes 12P in the second zone 12 in the wiring board 10A. The bottom electrodes 31P of the stacked device 30 are bonded to the third electrodes 13P in the third zone 13.

The image pickup module 1A has completely same advantages as the image pickup module 1. In other words, in the image pickup module according to the present invention, it is sufficient when the top electrodes 35P or the bottom electrodes 31P are bonded to the second zone 12, and the top electrodes 35P or the bottom electrodes 31P that are not bonded to the second zone 12 are bonded to the third zone 13.

For convenience of descriptions, terms "top/bottom" are used, but since the first side surface 30S1 becomes the top or the bottom depending on the observation direction, the top electrodes 35P and the bottom electrodes 31P turn into side surface electrodes.

Second Modification of First Embodiment

Figure 7:
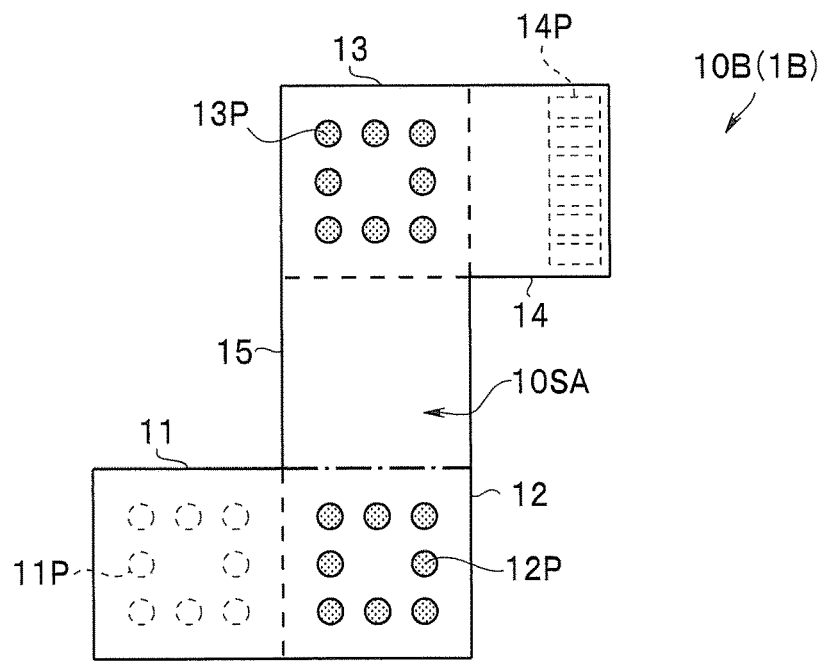
FIG. 7 is a development diagram of a wiring board of an image pickup module according to a second modification of the first embodiment.

A wiring board 10B of the image pickup module 1B according to the present modification illustrated in FIG. 7 has a shape symmetric to the wiring board 10 of the image pickup module 1.

Figure 8:
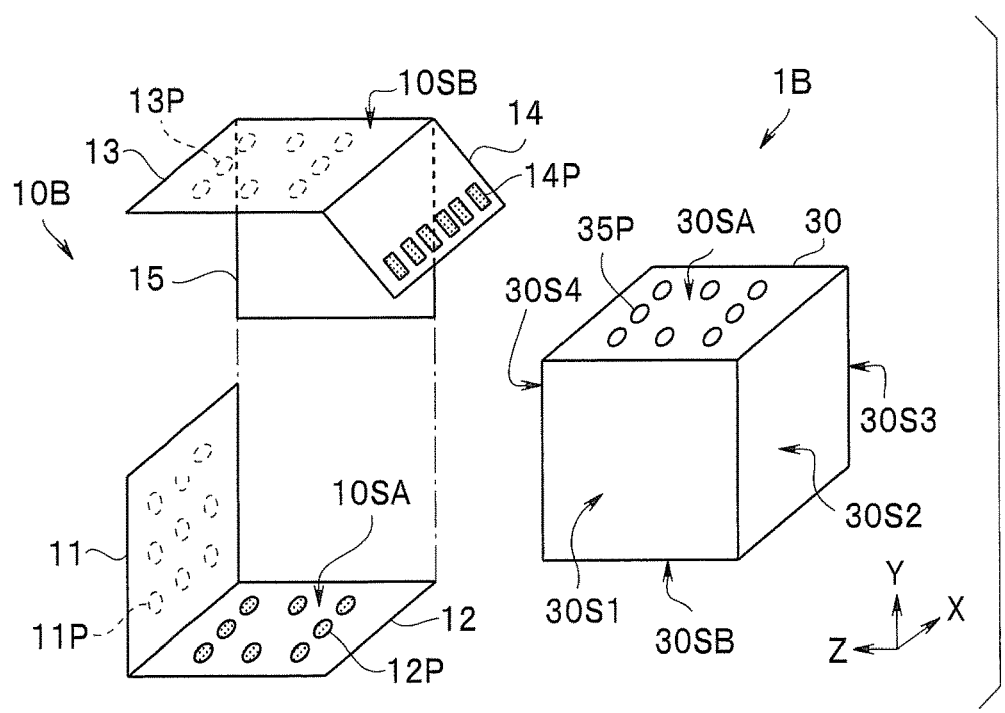
FIG. 8 is an exploded perspective view of a wiring board and a stacked device of the image pickup module according to the second modification of the first embodiment.

For this reason, in the wiring board 10B illustrated in FIG. 8, the fifth zone 15 is arranged on the third side surface 30S3 on a side opposite to the first side surface 30S1 of the stacked device 30.

In other words, according to the present invention, wiring boards of various modes can be used as long as the wiring board is a single wiring board in which a plurality of zones are consecutively disposed.

The top surface 30SA, the bottom surface 30SB, and the two side surfaces 30S1 and 30S3 including the first side surface 30S1 among the four side surfaces 30S1 to 30S4 are covered with the wiring board 10B in the stacked device 30.

Third Modification of First Embodiment

Figure 9:
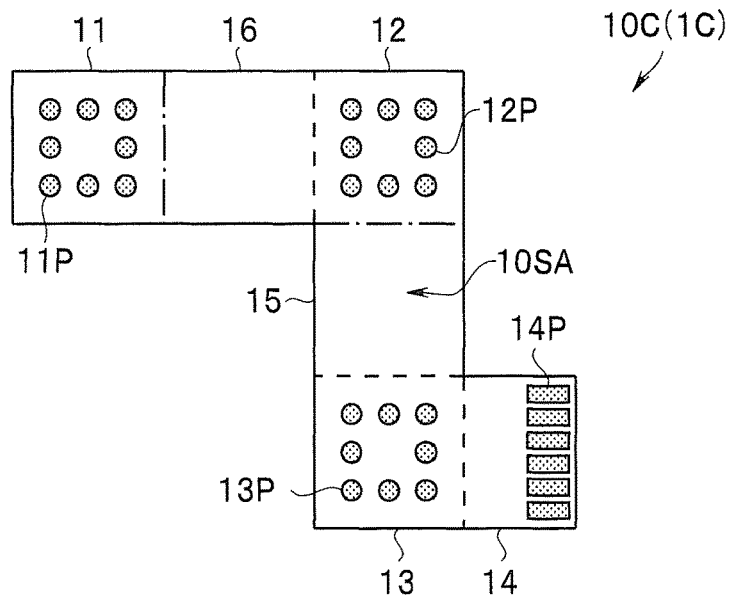
FIG. 9 is a development diagram of a wiring board of an image pickup module according to a third modification of the first embodiment.
Figure 10:
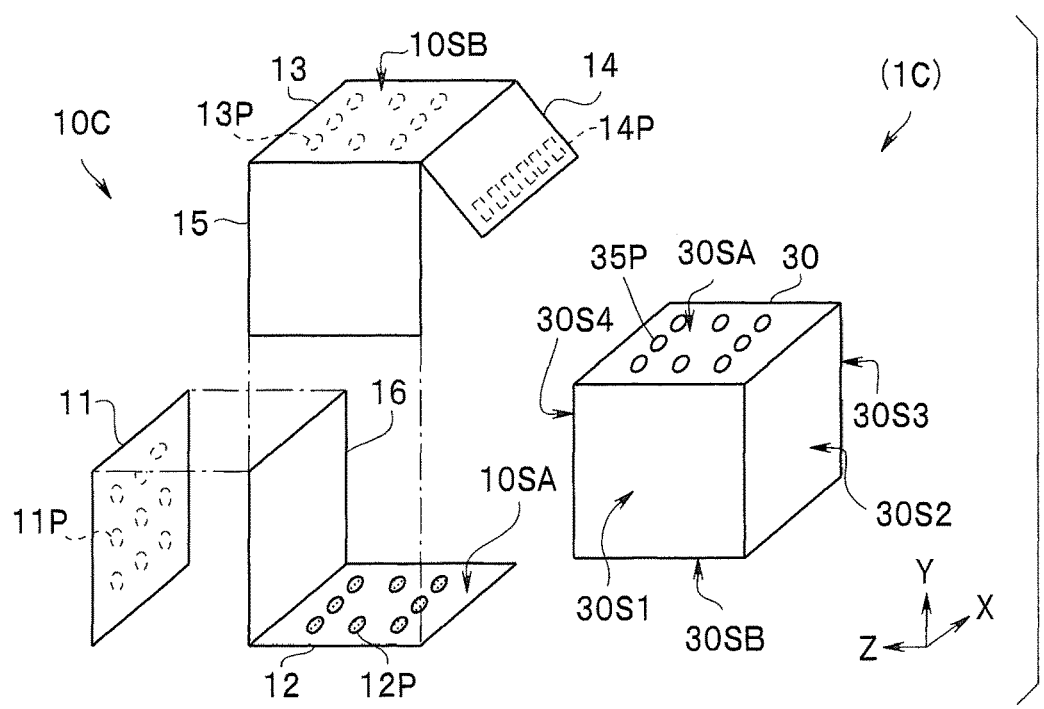
FIG. 10 is an exploded perspective view of the wiring board and a stacked device of the image pickup module according to the third modification of the first embodiment.

A wiring board 10C of the image pickup module 1C according to the present modification illustrated in FIGS. 9 and 10 further includes a sixth zone 16 disposed in an overlapping state with the first zone 11. The first zone 11, the sixth zone 16, the second zone 12, the fifth zone 15, the third zone 13, and the fourth zone 14 are consecutively disposed in the above-stated order.

The wiring board 10C is a one-sided wiring board on which the first electrodes 11P, the second electrodes 12P, the third electrodes 13P, the fourth electrodes 14P, and wiring that is not illustrated in the drawing are all disposed on the first main surface 10SA.

The wiring board 10C is fabricated more easily and inexpensively than the wiring board 10 serving as a double-sided wiring board or the like. For this reason, the image pickup module 1C is fabricated more easily and inexpensively than the image pickup module 1 or the like. Since the sixth zone 16 exists between the first zone 11 bonded to the imager 20 and the second zone 12 bonded to the stacked device 30 in the wiring board 10C, the imager 20 is hardly affected by heat.

The top surface 30SA, the bottom surface 30SB, two side surfaces 30S1 and 30S3 including the first side surface 30S1 among the four side surfaces 30S1 to 30S4 are covered with the wiring board 10C in the stacked device 30.

Fourth Modification of First Embodiment

Figure 11:
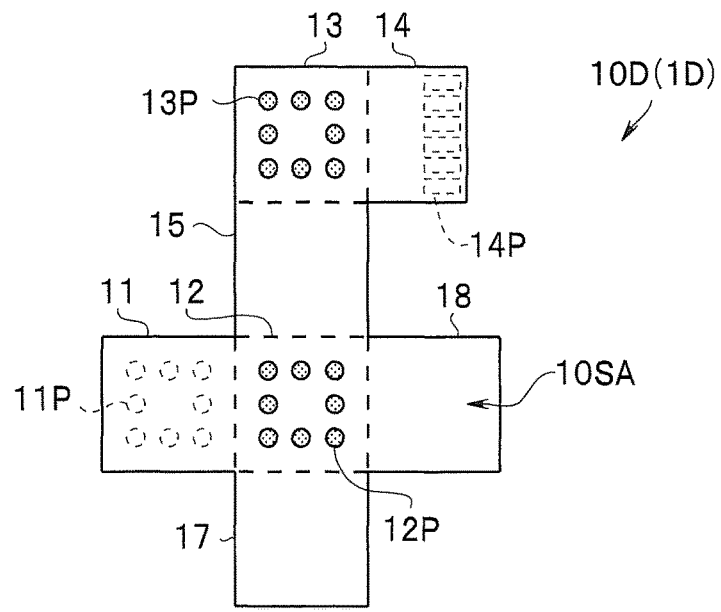
FIG. 11 is a development diagram of a wiring board of an image pickup module according to a fourth modification of the first embodiment.
Figure 12:
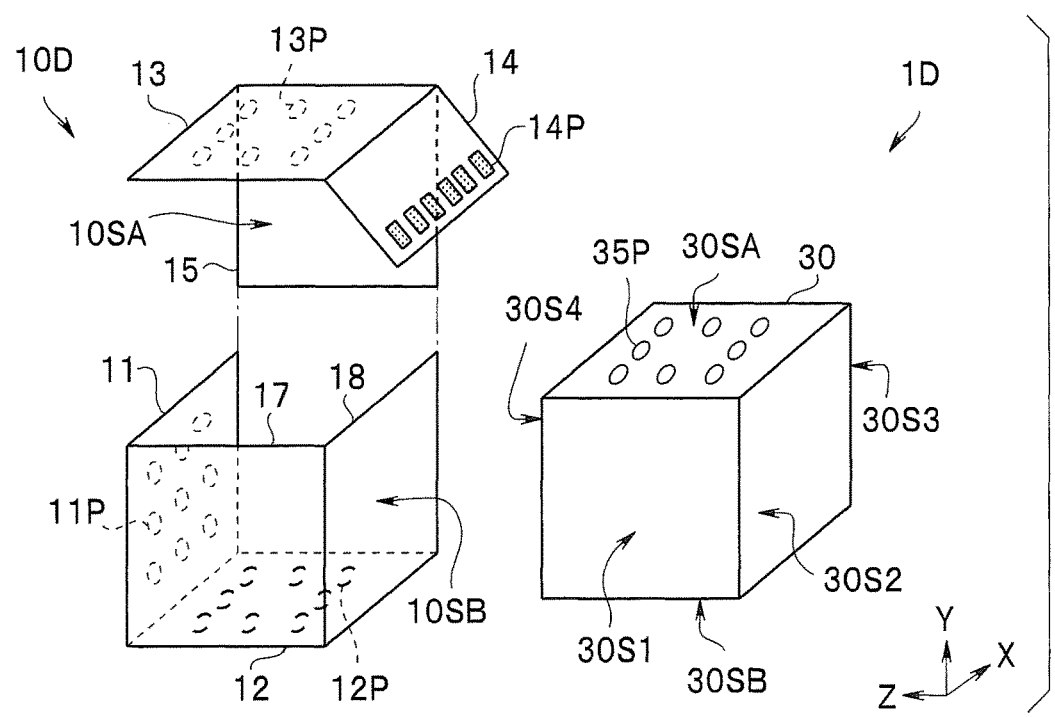
FIG. 12 is an exploded perspective view of the wiring board and a stacked device of the image pickup module according to the fourth modification of the first embodiment.

A wiring board 10D of the image pickup module 1D according to the present modification illustrated in FIGS. 11 and 12 further includes a seventh zone 17 and an eighth zone 18 in addition to the configuration of the wiring board 10B. The top surface 30SA, the bottom surface 30SB, and the four side surfaces 30S1 to 30S4 of the stacked device 30 are covered with the wiring board 10D.

Since the wiring board 10D functions as a barrier that prevents entry of moisture, the image pickup module 1D has higher reliability than the image pickup module 1 or the like.

Note that when a wiring board having a configuration similar to the wiring board 10 or 10C is used in the image pickup module 1D, needless to say, same advantages as the wiring board 10D are attained.

Fifth Modification of First Embodiment

Figure 13:
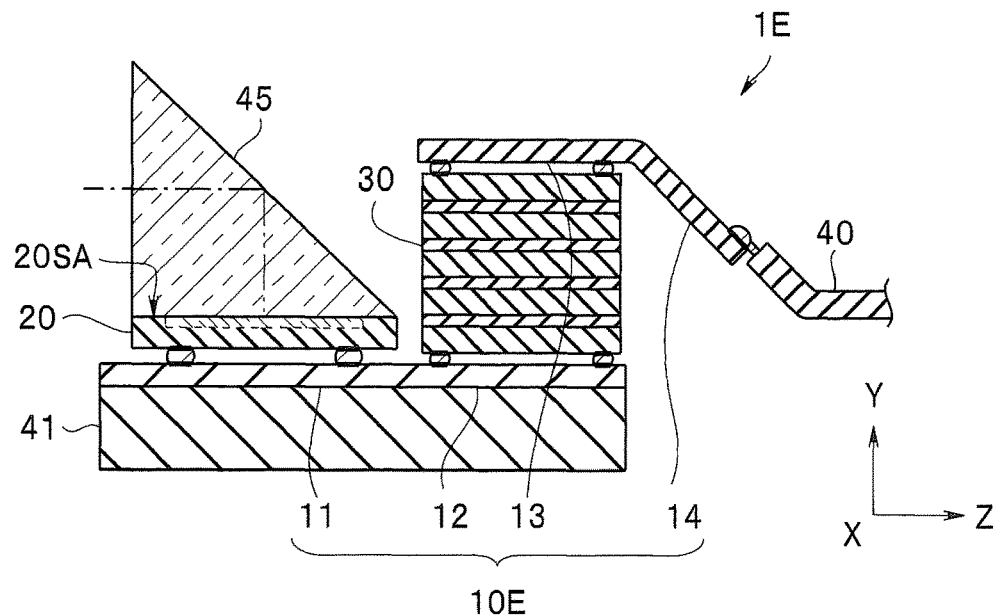
FIG. 13 is a cross sectional view of an image pickup module according to a fifth modification of the first embodiment.

The image pickup module 1E according to the present modification illustrated in FIG. 13 is of a transverse type including a prism 45.

A wiring board 10E has the same configuration as the wiring board 10, but no folded section exists between the first zone 11 and the second zone. In other words, according to the present invention, not all the sections between the zones in the wiring board necessarily need to be folded via folded sections.

In the image pickup module 1E, a wiring board 10E is fixed to a base substance 41 having no flexibility, but the base substance 41 is not an essential component.

Sixth Modification of First Embodiment

Figure 14:
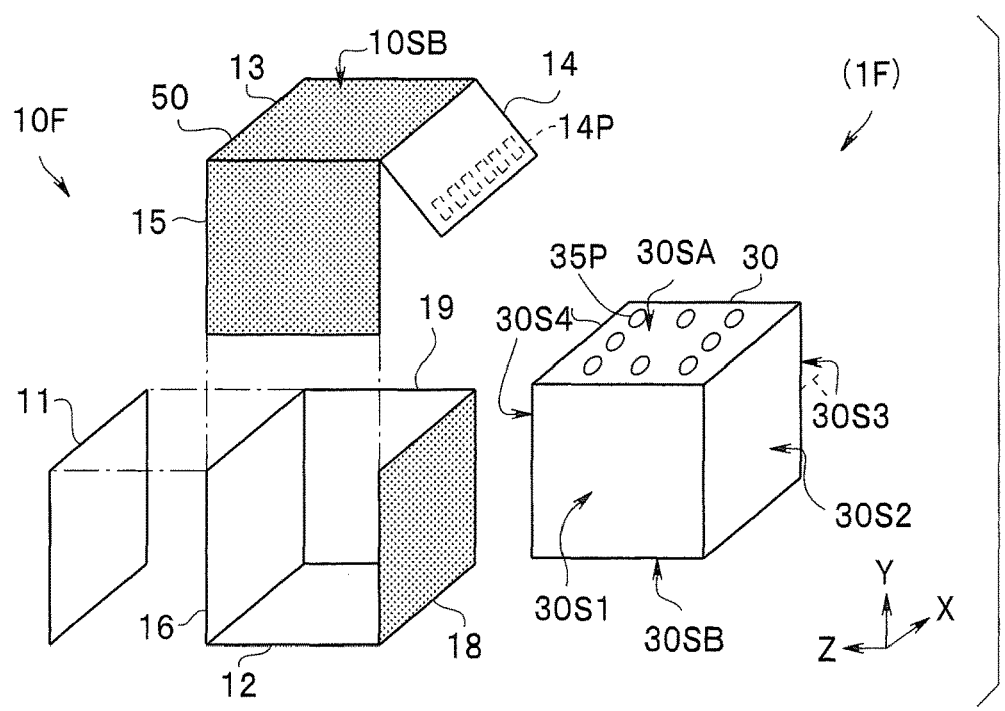
FIG. 14 is an exploded perspective view of a wiring board and a stacked device of an image pickup module according to a sixth modification of the first embodiment.

A wiring board 10F of the image pickup module 1F according to the present modification illustrated in FIG. 14 is similar to the wiring boards 10C and 10D. In other words, the wiring board 10F includes the sixth zone 16, which is arranged in an overlapped state with the first zone 11, the eighth zone 18, and a ninth zone 19. The top surface 30SA, the bottom surface 30SB, and the four side surfaces 30S1 to 30S4 of the stacked device 30 are covered with the wiring board 10F.

A metallic member 50 is further disposed on a rear surface of the first main surface 10SA on which the first electrodes 11P and the like are disposed, that is, the second main surface 10SB serving as an external surface. The metallic member 50 is a film having a same component as a conductive film that configures wiring (not illustrated) of the wiring board 10F, for example, a copper film.

Note that when the first electrodes 11P and the like are all disposed on the first main surface 10SA in the wiring board 10C, wiring may also be disposed in the intermediate layer between the first main surface 10SA and the second main surface 10SB.

Since the stacked device 30 is covered with the metallic member 50 having a radiation effect and a shielding effect, the image pickup module 1F has higher reliability than the image pickup module 1A.

Note that a metallic member serving as a different member may also be affixed to the external surface of the wiring board.

The metallic member 50 may also be disposed in only part of the zones, but the metallic member 50 is most preferably disposed in all the zones that surround the stacked device 30.

Seventh Modification of First Embodiment

Figure 15:
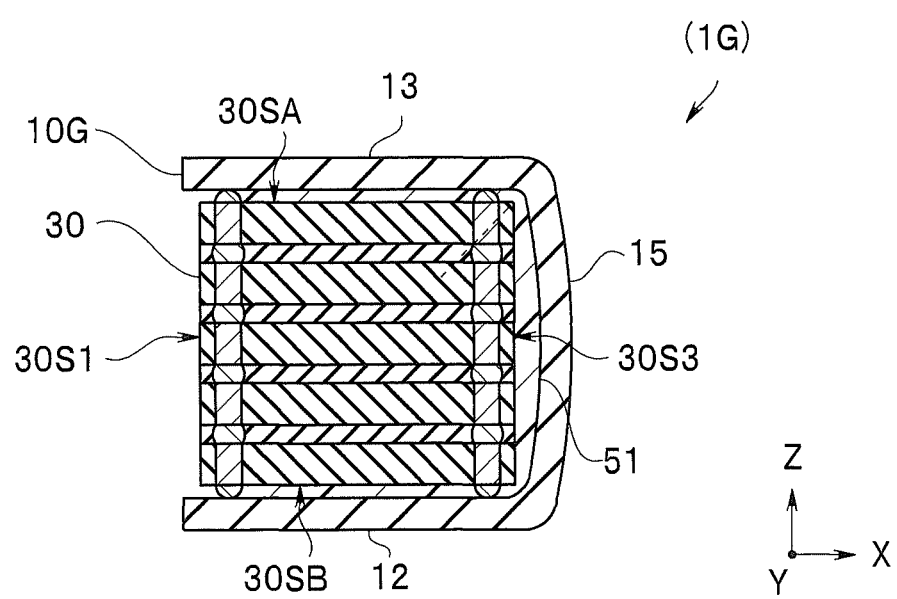
FIG. 15 is a cross sectional view of a wiring board and a stacked device of an image pickup module according to a seventh modification of the first embodiment.

The image pickup module 1G illustrated in FIG. 15 includes resin 51 between the side surface 30S3 of the stacked device and the fifth zone 15 of a wiring board 10G. The resin 51 is disposed on the side surface 30S3 of the stacked device, and an external surface of the resin 51 constitutes a convex curved surface. It may be not easy to dispose the wiring board 10G on the side surface of the ultra-compact stacked device 30 in parallel in some cases. In the image pickup module 1G, since the wiring board 10G can be disposed along the curved resin 51, fabrication is easy.

Since the resin 51 composed of epoxy resin or the like suppresses transmission of moisture, the image pickup module 1G has high reliability.

Note that the resin 51 may also be disposed on the top surface 30SA, the bottom surface 30SB, and the side surfaces of the stacked device 30 also in the image pickup module 1 or the like. Note, however, that external surfaces of the resin 51 on the top surface 30SA and the bottom surface 30SB also turn into flat surfaces.

As described above, it is sufficient when the top surface 30SA, the bottom surface 30SB, and at least two side surfaces including the first side surface 30S1 among the four side surfaces 30S1 to 30S4 are covered with the wiring board in the stacked device. It is sufficient when the signal cable is bonded to a zone other than the first zone of the wiring board.

Second Embodiment

Figure 16:
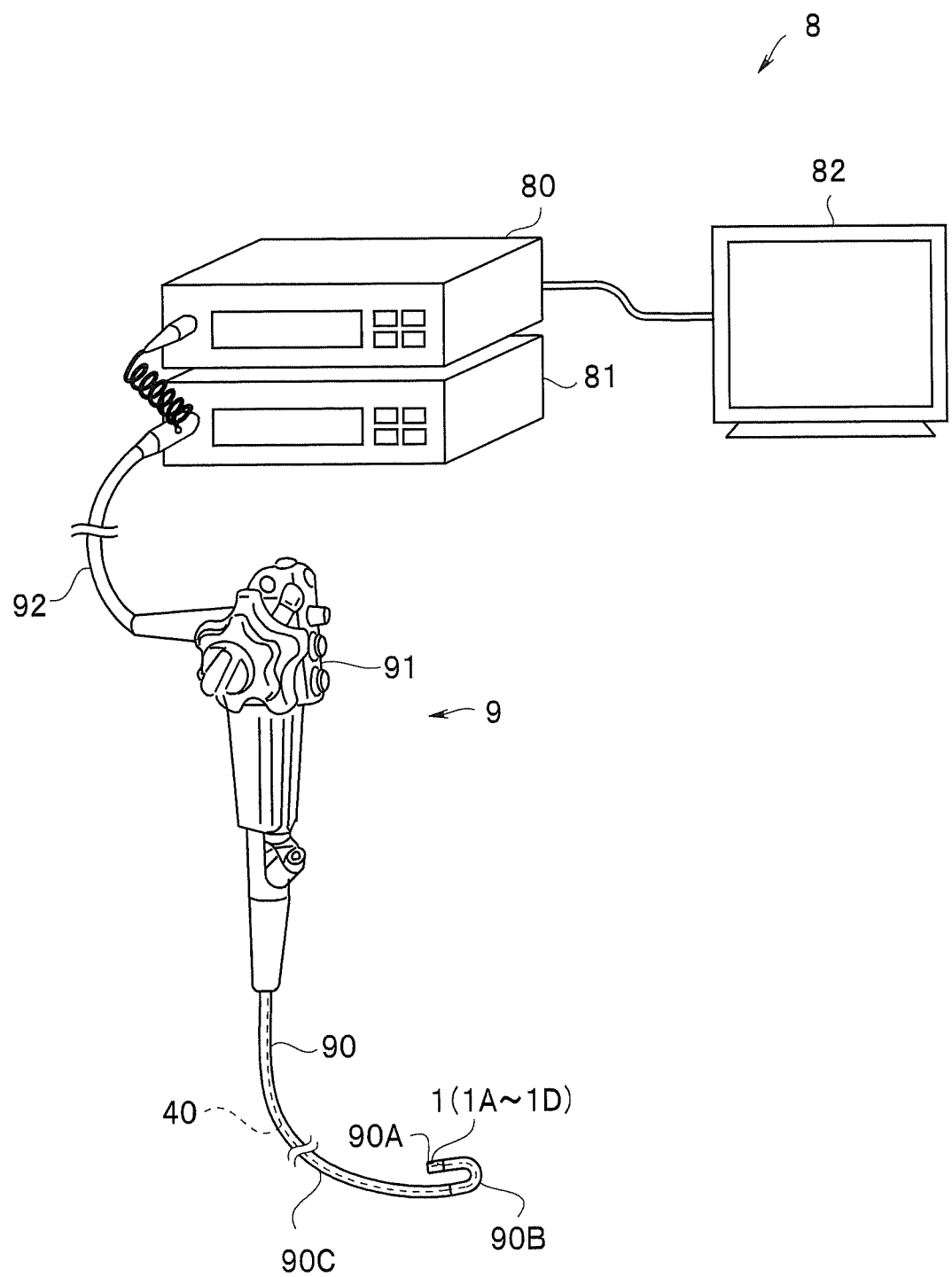
FIG. 16 is a perspective view of an endoscope system including an endoscope according to a second embodiment.

An endoscope system 8 including an endoscope 9 according to the present embodiment illustrated in FIG. 16 includes the endoscope 9, a processor 80, a light source apparatus 81, and a monitor 82. The endoscope 9 includes an insertion portion 90, an operation portion 91, and a universal cord 92.

The endoscope 9 outputs an image signal when the insertion portion 90 is inserted into a body cavity of an object and shoots an internal body image of the object.

The insertion portion 90 is configured by a distal end portion 90A in which the image pickup module 1 or the image pickup module 1A to 1G (hereinafter, referred to as the image pickup module 1 or the like) is disposed, a freely bendable bending portion 90B consecutively disposed on a proximal end side of the distal end portion 90A, and a flexible portion 90C consecutively disposed on a proximal end side of the bending portion 90B. The bending portion 90B bends in accordance with an operation of the operation portion 91.

The operation portion 91 in which various types of buttons for operating the endoscope 9 are provided is disposed on a proximal end side of the insertion portion 90 of the endoscope 9.

The light source apparatus 81 includes a white LED, for example. Illumination light outputted by the light source apparatus 81 is guided to the distal end portion 90A via a light guide (not illustrated) that allows insertion of the universal cord 92 and the insertion portion 90 to illuminate the object.

The endoscope 9 includes the insertion portion 90, the operation portion 91, and the universal cord 92, and transmits image pickup signals outputted by the image pickup module 1 and the like disposed in the distal end portion 90A of the insertion portion 90 through the signal cable 40 that allows insertion of the insertion portion 90.

Since the image pickup module 1 or the like is ultra compact, the distal end portion 90A of the insertion portion 90 has a small diameter, and the endoscope 9 is less invasive. Since the image pickup module 1 or the like performs the primary processing on the image pickup signal outputted by the imager by the stacked device 30 arranged immediately proximal to the imager, the endoscope 9 displays a high quality image. In the image pickup module 1 or the like, since the imager 20 is hardly damaged by heat at the time of fabrication, the endoscope 9 has high reliability.

Note that the endoscope 9 is described by using a flexible endoscope as an example, but the endoscope 9 may also be a rigid endoscope or a capsule-type endoscope that does not include a signal cable.

The present invention is not limited to the above-mentioned embodiments and the like, and various modifications, alterations, and the like can be made in a range without changing the gist of the present invention.

What is claimed is:

1. An endoscope comprising an image pickup apparatus, the image pickup apparatus comprising:
   an imager comprising:
      a light receiving surface;
      a rear surface on a reverse side of the light receiving surface; and
      an external electrode disposed on the rear surface;
   a stacked device comprising:
      a plurality of devices stacked in a direction intersecting an optical axis of the imager
      the stacked device having a rectangular parallelepiped shape including a top surface, a bottom surface on an opposite side to the top surface, and four side surfaces; and
      a top electrode disposed on the top surface and a bottom electrode disposed on the bottom surface;
   a signal cable; and
   a three-dimensional wiring board folded from a single flat sheet, the wiring board including a first zone, a second zone, a third zone, a fourth zone, and a fifth zone, wherein
      the first zone, the second zone, the fifth zone, the third zone, and the fourth zone, each of which has a rectangular shape, are disposed in the above-stated order when in a form of the single flat sheet,
      the second zone, the fifth zone, and the third zone are disposed in a serial direction when in the form of the single flat sheet,
      the first zone and the second zone are disposed in a first direction orthogonal to the serial direction when in the form of the single flat sheet,
      the third zone and the fourth zone are disposed in a second direction opposite to the first direction when in the form of the single flat sheet,
      the wiring board is folded via a first folded section between the first zone and the second zone, a second folded section between the second zone and the fifth zone, a third folded section between the fifth zone and the third zone, and a fourth folded section between the third zone and the fourth zone,
      the first zone includes a first electrode to which the external electrode of the imager is bonded,
      the second zone includes a second electrode to which one of the top electrode or the bottom electrode of the stacked device is bonded,
      the third zone includes a third electrode to which an other of the top electrode or the bottom electrode of the stacked device is bonded,
      the fourth zone includes a fourth electrode to which the signal cable is bonded, and
      the fifth zone is arranged on a first side surface among the four side surfaces of the stacked device,
   wherein the top surface, the bottom surface, and at least two side surfaces including the first side surface among the four side surfaces are covered with the wiring board in the stacked device.

2. The endoscope according to claim 1, wherein
   the wiring board further includes a sixth zone having a rectangular shape and arranged between the first zone and the second zone, and
   the first zone and the sixth zone are arranged in an overlapped state.

3. The endoscope according to claim 1, wherein
   the wiring board further includes a sixth zone and a seventh zone,
   the sixth zone is disposed on the opposite side of the fifth zone across the second zone,
   the seventh zone is disposed on the opposite side of the first zone across the second zone,
   the sixth zone and the seventh zone are folded with respect to the second zone, and
   the top surface, the bottom surface, and the four side surfaces of the stacked device are covered with the wiring board.

4. The endoscope according to claim 1, further comprising: a metallic member disposed on an external surface of at least one of the zones of the wiring board.

5. The endoscope according to claim 4, wherein the metallic member is disposed in all zones that surround the stacked device.

6. The endoscope according to claim 4, wherein the metallic member is a film including a same component as a conductive film of the wiring board.

7. The endoscope according to claim 1, wherein a section between a zone of the wiring board which is arranged on a side surface of the stacked device and the stacked device is filled with resin including an external surface constituted by a curved surface.

8. An image pickup apparatus comprising:
an imager comprising:
a light receiving surface;
a rear surface on a reverse side of the light receiving surface; and
an external electrode disposed on the rear surface;
a stacked device comprising:
a plurality of devices stacked in a direction intersecting an optical axis of the imager;
the stacked device having a rectangular parallelepiped shape including a top surface, a bottom surface on an opposite side to the top surface, and four side surfaces; and
a top electrode disposed on the top surface and a bottom electrode disposed on the bottom surface;
a signal cable; and
a three-dimensional wiring board folded from a single flat sheet, the wiring board including a first zone, a second zone, a third zone, a fourth zone, and a fifth zone, wherein
the first zone, the second zone, the fifth zone, the third zone, and the fourth zone, each of which has a rectangular shape, are disposed in the above-stated order when in a form of the single flat sheet,
the second zone, the fifth zone, and the third zone are disposed in a serial direction when in the form of the single flat sheet,
the first zone and the second zone are disposed in a first direction orthogonal to the serial direction when in the form of the single flat sheet,
the third zone and the fourth zone are disposed in a second direction opposite to the first direction when in the form of the single flat sheet,
the wiring board is folded via a first folded section between the first zone and the second zone, a second folded section between the second zone and the fifth zone, a third folded section between the fifth zone and the third zone, and a fourth folded section between the third zone and the fourth zone,
the first zone includes a first electrode to which the external electrode of the imager is bonded,
the second zone includes a second electrode to which one of the top electrode or the bottom electrode is bonded,
the third zone includes a third electrode to which an other of the top electrode or the bottom electrode is bonded,
the fourth zone includes a fourth electrode to which the signal cable is bonded, and
the fifth zone is arranged on a first side surface among the four side surfaces of the stacked device,
wherein the top surface, the bottom surface, and at least two side surfaces including the first side surface among the four side surfaces are covered with the wiring board in the stacked device.

9. The image pickup apparatus according to claim 8, wherein
the wiring board further includes a sixth zone having a rectangular shape and arranged between the first zone and the second zone, and
the first zone and the sixth zone are arranged in an overlapped state.

10. The image pickup apparatus according to claim 8, wherein
the wiring board further includes a sixth zone and a seventh zone,
the sixth zone is disposed on the opposite side of the fifth zone across the second zone,
the seventh zone is disposed on the opposite side of the first zone across the second zone,
the sixth zone and the seventh zone are folded with respect to the second zone, and
the top surface, the bottom surface, and the four side surfaces of the stacked device are covered with the wiring board.

11. The image pickup apparatus according to claim 8, further comprising:
a metallic member disposed on an external surface of at least one of the zones of the wiring board.

12. The image pickup apparatus according to claim 11, wherein the metallic member is disposed in all zones that surround the stacked device.

13. The image pickup apparatus according to claim 11, wherein the metallic member is a film including a same component as a conductive film of the wiring board.

14. The image pickup apparatus according to claim 8, wherein a section between a zone of the wiring board which is arranged on a side surface of the stacked device and the stacked device is filled with resin including an external surface constituted by a curved surface.

* * * * *